United States Patent [19]

Balzer et al.

[11] Patent Number: 5,542,953
[45] Date of Patent: Aug. 6, 1996

[54] 5-HALOGEN-2,4-BIS(ALKYLAMINO)-1-ALKYLBENZENES AND HAIR DYE COMPOSITIONS CONTAINING SAME

[75] Inventors: Wolfgang R. Balzer; Thomas Clausen, both of Alsbach; Anke Frank, Frankfurt; Alexa Weinges, Heidelberg, all of Germany

[73] Assignee: Wella AG, Darmstadt, Germany

[21] Appl. No.: 142,492

[22] PCT Filed: Jan. 7, 1993

[86] PCT No.: PCT/EP93/00011

§ 371 Date: Oct. 22, 1993

§ 102(e) Date: Oct. 22, 1993

[87] PCT Pub. No.: WO93/16677

PCT Pub. Date: Sep. 2, 1993

[30] Foreign Application Priority Data

Feb. 29, 1992 [DE] Germany ............... 42 06 416.3

[51] Int. Cl.$^6$ ............ A61K 7/13; C07C 211/51; C07C 211/52
[52] U.S. Cl. ............ 8/416; 8/406; 8/407; 8/408; 8/411; 8/412; 8/615; 8/616; 564/305; 564/442
[58] Field of Search ............... 8/405, 406, 407, 8/408, 410, 411, 412, 416, 614, 615, 616; 564/306, 442, 305

[56] References Cited

U.S. PATENT DOCUMENTS

| 3,857,674 | 12/1974 | Forsthoff et al. ............ 8/416 |
| 4,145,364 | 3/1979 | Mulvey et al. ............ 564/442 |
| 4,566,876 | 1/1986 | Brown et al. ............ 8/411 |
| 5,143,518 | 9/1992 | Madrange ............ 8/406 |

FOREIGN PATENT DOCUMENTS

| 2112550 | 6/1972 | France . |
| 1937230 | 1/1970 | Germany . |
| 1492167 | 9/1972 | Germany . |
| 3430513 | 2/1986 | Germany . |
| 3622784 | 1/1988 | Germany . |
| 3724642 | 2/1989 | Germany . |
| 60-193950 | 10/1985 | Japan . |
| 1321560 | 6/1973 | United Kingdom . |
| 2176494 | 12/1986 | United Kingdom . |
| 9204005 | 3/1992 | WIPO . |

Primary Examiner—Paul Lieberman
Assistant Examiner—Caroline L. Dusheck
Attorney, Agent, or Firm—Michael J. Striker

[57] ABSTRACT

The composition for the oxidative dyeing of hair contains at least one coupler of the general formula

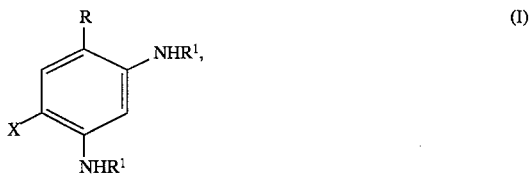

where R is a straight-chain or branched $C_1$- to $C_4$-alkyl group, X is chlorine or fluorine, and $R^1$ is a straight-chain or branched $C_1$- to $C_4$-alkyl group or a straight-chain or branched $C_2$- to $C_4$-hydroxyalkyl group. The 5-halogen-2,4-bis(alkylamino)-1-alkylbenzenes of the formula (I) are novel. The couplers of the general formula (I) may be obtained through simple chemical reactions, are easily soluble in water and have an outstanding shelf stability, in particular as a constituent of the hair dye composition described here. The dyeing results which can be achieved with the hair dye composition according to the invention are particularly distinguished by the color intensity of the red hues, in addition to the multitude of shades, and by a good purity of color with respect to blue hues.

14 Claims, No Drawings

5-HALOGEN-2,4-BIS (ALKYLAMINO)-1-ALKYLBENZENES AND HAIR DYE COMPOSITIONS CONTAINING SAME

BACKGROUND OF THE INVENTION

The subject matter of the invention is a composition for the oxidative dyeing of hair based on 5-halogen-2,4-bis-(alkylamino)- 1-alkylbenzenes as couplers and new 5-halogen- 2,4-bis(alkylamino)-1-alkylbenzenes.

Oxidative dyes have achieved considerable importance in hair dyeing practice. The dyes are produced by oxidative coupling of developers and couplers in the hair shaft. This leads to very intensive hair colorings with very good color fastness. Moreover, different shades can be produced by combining suitable developers and couplers.

Preferably, 2,5-diaminotoluene, 1,4-diaminobenzene, 2-(2'-hydroxyethyl)-1,4-diaminobenzene, 4-aminophenol, 4-amino-2-aminomethylphenol, and 4-amino-3-methylphenol are used as developers.

Preferred couplers include m-phenylenediamine and its derivatives such as 2,4-diaminophenoxyethanol, 2,4-diaminobenzyl alcohol, 2-amino-4-(2'-hydroxyethyl)aminoanisole or pyridine derivatives such as 3,5-diamino-2,6-dimethoxypyridine as blue coupler, 1-naphthol, m-aminophenol and its derivatives such as 2-amino-4-chloro-6-methylphenol, 3-amino-2-methylphenol, 4-amino-2-hydroxyphenoxyethanol, and 3-amino-5-hydroxy-2,6-dimethoxypyridine as red couplers, as well as resorcinol, 4-chlororesorcinol, 4,6-dichlororesorcinol, 2-methylresorcinol, 4-hydroxy-1,2-methylenedioxybenzene, 4-(2'-hydroxyethyl)amino-1,2-methylenedioxybenzene, and 4-hydroxyindole as couplers for the brown-blond range.

There are numerous special requirements demanded of oxidative dyes which are used for dyeing human hair. For example, they must be unobjectionable in toxicological and dermatological respects and must enable the desired intensity of coloring. In addition, a favorable fastness to light, permanent waving, acids and rubbing are required of the achieved hair colorings. But, in every instance, such hair coloring must remain stable over a period of at least 4 to 6 weeks without being affected by light, rubbing or chemical agents. Moreover, it must be possible for a wide assortment of different shades to be produced by combining suitable developers and couplers.

However, the couplers currently used in hair dyes to achieve the red and clear blue shades in particular cannot satisfy all of the requirements specified above.

The 2,4-diamino-5-tetrafluoroethoxytoluene known from DE-OS 34 30 513 shows no mutagenicity in the Ames test, but the depth of color and light fastness of the colorings achieved with this coupler are not satisfactory.

The couplers 2,4-diamino-5-ethoxytoluene and 2,4-diamino- 5-(2'-hydroxyethyl)oxytoluene described in DE-OS 36 22 784 possess good toxicological characteristics, but the coloring achieved by them with developers such as p-aminophenol or its derivatives are very washed out.

SUMMARY OF THE INVENTION

Therefore, it is an object of the present invention to provide a hair dye composition for the oxidative dyeing of hair which is based on conventional developers for dyeing hair, contains new couplers, and which satisfies the requirements mentioned above with respect to the technical characteristics of the new couplers in terms of application.

It has now been found that the proposed problem is solved in an outstanding manner by a composition for the oxidative dyeing of hair based on a combination of developers and couplers and, as needed, other dye components and conventional additives in hair dye compositions which contains at least one coupler of the general formula

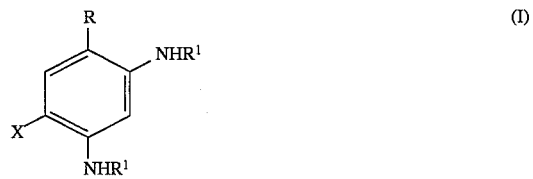

where R is a straight-chain or branched $C_1$- to $C_4$-alkyl group, X is chlorine or fluorine, and $R^1$ is a straight-chain or branched $C_1$- to $C_4$-alkyl group or a straight-chain or branched $C_2$- to $C_4$-hydroxyalkyl group, or its physiologically tolerated water-soluble salt.

The couplers of the general formula (I) may be obtained through simple chemical reactions from technically accessible starting compounds and, together with developers such a p-phenylenediamine, result in clear blue colorings without a reddish cast. With developers such as p-aminophenol, color-saturated red coloring can be achieved whose intensity is even greater than that achieved in coloring with 2,4-diaminotoluene without substitutions.

The couplers of the general formula (I) are easily soluble in water and have an outstanding shelf stability particularly as constituents of the hair dye composition described here.

The couplers of formula (I) according to the invention are contained in the hair dye composition described here in amounts sufficient for dyeing the hair, preferably in quantities of 0.01 to 5 percent by weight, but particularly 0.1 to 3 percent by weight.

The couplers of the general formula (I) contained in the hair dye composition are preferably 5-fluoro-2,4-bis-(methylamino)toluene, 5-fluoro-2,4-bis(ethylamino)toluene, 5-fluoro-2,4-bis[(2'-hydroxyethyl)amino]toluene, and 5-chloro-2,4-bis[(2'-hydroxyethyl)amino]toluene.

Moreover, the hair dye composition can also contain 0.01 to 5 percent by weight, preferably 0.1 to 3 percent by weight, of at least one other coupler such as resorcinol, 4-chlororesorcinol, 4,6-dichlororesorcinol, 2-methylresorcinol, 2-amino-4-(2'-hydroxyethyl)aminoanisole, 2-amino-4-ethylaminoanisole, 2,4-diaminobenzyl alcohol, m-phenylenediamine, 5-amino-2-methylphenol, 2,4-diaminophenoxyethanol, 1-naphthol, m-aminophenol, 3-amino-4-chloro-6-methylphenol, 3-amino-2-methylphenol, 4-amino-2-hydroxyphenoxyethanol, 4-hydroxy-1,2-methylenedioxybenzene, 4-(2'-hydroxyethylamino)- 1,2-methylenedioxybenzene, 2,4-diamino-5-ethoxytoluene, 4-hydroxyindole, 3-amino-5-hydroxy-2,6-dimethoxypyridine, and 3,5-diamino-2,6-dimethoxypyridine.

The following developers in particular may be selected as constituents of the hair dye composition according to the invention: 1,4-diaminobenzene, 2,5-diaminotoluene, 2,5-diaminobenzyl alcohol, 2-(2'-hydroxyethyl)-1,4-diaminobenzene, 4-aminophenol, 4-amino-2-aminomethylphenol, 4-amino-3-methylphenol, 4-amino-2-methoxymethylphenol, 4-amino-2-ethoxymethylphenol, and tetraaminopyrimidine or their physiologically tolerated salts. The quantity of developers contained in the composition according to the invention is preferably 0.01 to 5 percent by weight, but particularly 0.1 to 3.0 percent by weight.

The conventional couplers and developers can be contained in the hair dye composition according to the invention individually or in combination with one another. The total quantity of combined developer and couplers contained in the hair dye composition described here is approximately 0.1 to 5.0 percent by weight, preferably 0.5 to 4.0 percent by weight.

The developers are generally used in approximately equimolar amounts with respect to the couplers. However, it is not disadvantageous in this respect if the quantity of developers is somewhat greater or less than that of the couplers.

Further, the hair dye composition of the present application can also contain other dyeing components, e.g. 6-amino-2-methylphenol and 2-amino-5-methylphenol, as well as conventional direct dyes, e.g. triphenylmethane dyes, such as Basic Violet 14 (C.I. 42,510) (4-{(4'-aminophenyl)-(4"-imino-2",5"-cyclohexadien-1"-yliden)methyl}-2-methylaminobenzene monohydrochloride) and Basic Violet 2 (C.I. 42,520) (4-{(4'-amino-3'-methylphenyl)-(4"-imino-3"-methyl-2",5"-cyclohexadien-1"-yliden)methyl}-2-methylaminobenzene monohydrochloride), aromatic nitro dyes such as 2-nitro-1,4-diaminobenzene, 2-amino-4-nitrophenol, 2-amino-5-nitrophenol, 2-amino-4,6-dinitrophenol, 2-amino-5-(2'-hydroxyethyl)aminonitrobenzene and 4-(2'-hydroxyethylamino)-3-nitrotoluene, 1-(2'-ureidoethyl)amino-4-nitrobenzene and azo dyes such as Acid Brown 4 (C.I. 14,805) (7-{( 4'-aminophenyl)azo}-8-hydroxynaphthalene 4-sulfonic acid sodium salt) and dispersed dyes such as 1,4-diaminoanthraquinone and 1,4,5,8-tetraaminoanthraquinone.

Other suitable dyes which are absorbed directly in hair are described e.g. in J. C. Johnson, "Hair Dyes", Noyes Data Corp., Park Ridge, U.S.A (1973), pages 3–91 and 113–139 (ISBN: 0-8155-0477-2).

Of course, the couplers and developers, as well as the other dye components insofar as they are bases, can also be used in the form of physiologically tolerated acid addition salts such as hydrochloride or sulfate or—insofar as they have aromatic OH groups—in the form of salts with bases such as alkali phenolates.

Further, the hair dye composition can contain direct dyes and self-coupling dye precursors in quantities of 0.1 to 4.0 percent by weight.

Other conventional cosmetic ingredients can also be contained in the hair dye composition, e.g. antioxidants such as ascorbic acid, thiogylcolic acid or sodium sulfite, and perfume oils, complexing agents, wetting agents, emulsifiers, thickeners and hair care materials, etc.

The preparation form can be e.g. a solution, particularly an aqueous-alcoholic solution. But the particularly preferred preparation forms are creams, gels or emulsions. It is composed of a mixture of dye components and the usual ingredients for such preparations.

Conventional ingredients in solutions, creams, emulsions or gels are e.g. solvents such as water, lower aliphatic alcohols, e.g. ethanol, propanol and isopropanol or glycols such as glycerin and 1,2-propylene glycol, wetting agents or emulsifiers from the classes of anionic, cationic, amphoteric or nonionic surface-active substances such as fatty alcohol sulfates, ethoxylated fatty alcohol sulfates, alkyl sulfonates, alkylbenzene sulfonates, alkyltrimethylammonium salts, alkyl betaines, ethoxylated fatty alcohols, ethoxylated nonylphenols, fatty acid alkanol amides, ethoxylated fatty acid esters, and thickeners such as higher fatty alcohols, starch, cellulose derivatives, petrolatum, paraffin oil and fatty acids, as well as hair care materials such as cationic resins, lanolin derivatives, cholesterol, pantothenic acid and betaine. The aforementioned components are used in conventional quantities for such purposes. For example, the wetting agents and emulsifiers are used in concentrations of approximately 0.5 to 30 percent by weight, the thickeners are used in quantities of approximately 0.1 to 25 percent by weight and the hair care materials are used in concentrations of approximately 0.1 to 5.0 percent by weight.

Depending on the composition, the hair dye composition according to the invention can react in a slightly acidic, neutral or alkaline manner. In particular, it has a pH in the alkaline range between 8.0 and 11.5 and is preferably adjusted with ammonia. However, organic amines such as monoethanolamine and triethanolamine or inorganic bases such as sodium hydroxide and potassium hydroxide can also be used.

When applied for oxidative dyeing of hair, the aforementioned hair dye composition is mixed immediately prior to use with an oxidizing agent and a quantity of this mixture sufficient for the hair dyeing treatment, generally approximately 60 to 200 g depending on the fullness of the hair, is applied to the hair.

Hydrogen peroxide or its addition compounds in urea, melamine or sodium borate in the form of a 3- to 12-percent aqueous solution, preferably a 6-percent aqueous solution, are the principle oxidizing agents selected for the development of the hair coloring.

If a 6-percent hydrogen peroxide solution is used as oxidizing agent, the weight ratio of hair dye composition to oxidizing agent is 5:1 to 1:2, but preferably 1:1. Larger quantities of oxidizing agent are used in the hair dye composition chiefly when there are higher concentrations of dyestuff or when a more intensive bleaching of the hair is intended simultaneously.

The mixture is allowed to act on the hair at 15° to 50° C. for approximately 10 to 45 minutes, preferably 30 minutes; the hair is then rinsed with water and dried. The hair is washed with a shampoo after this rinse, if necessary, and possibly re-rinsed with a weak organic acid such as citric acid or tartaric acid. The hair is then dried.

The hair dye composition according to the invention results in hair coloring with excellent color fastness, particularly light fastness, washing fastness and rubbing fastness, and can be removed again by reducing agents. With respect to dyeing possibilities, the hair dye composition according to the invention offers a wide assortment of different shades depending on the type and composition of dye components. The high intensity of reds and color purity of blues which can be achieved are remarkable.

Finally, graying hair which has not already been chemically damaged can also be dyed easily and with good covering power with the described hair dye composition according to the present application. The achieved coloring can be reproduced easily in a consistent manner regardless of different hair textures.

The 5-halogen-2,4-bis(alkylamino)-1-alkylbenzene of the general formula (I) can be produced in a simple manner from the corresponding industrially accessible 3-halogenalkylbenzenes. The corresponding 5-halogen-2,4-diaminoalkylbenzene (IV) according to the following diagram,

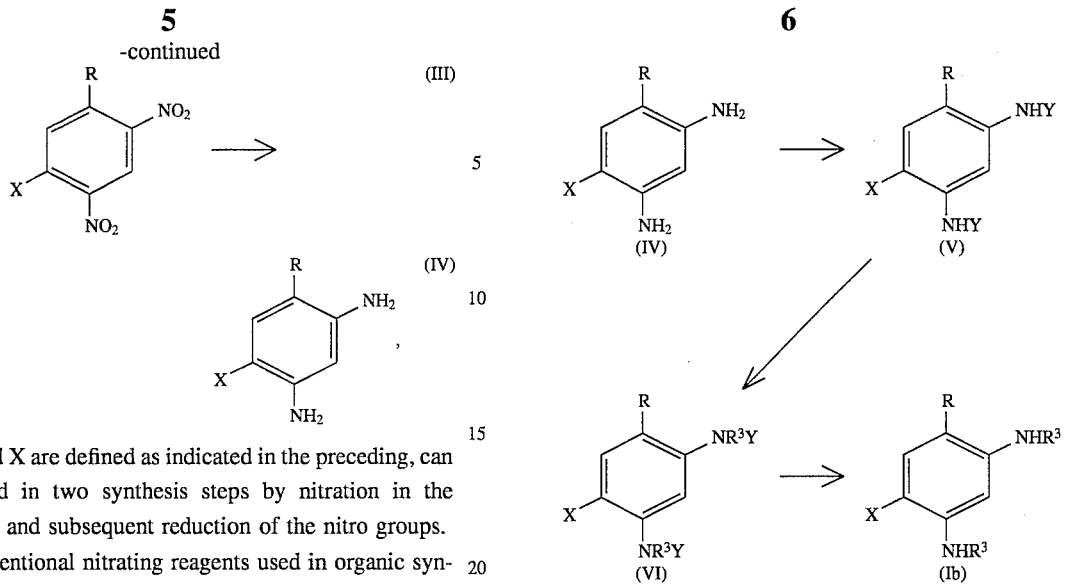

where R and X are defined as indicated in the preceding, can be produced in two synthesis steps by nitration in the 2,4-position and subsequent reduction of the nitro groups.

The conventional nitrating reagents used in organic synthesis can be used for this nitration, preferably a mixture of sulfuric acid and nitric acid. As to the reduction of the nitro groups, the known reagents for this synthesis step, e.g. hydrogen in the presence of a suitable catalyst, can be used.

Proceeding from the 5-halogen-2,4-diaminoalkylbenzene (IV), the new couplers of the general formula (I) are obtainable in two ways:

1. The 5-halogen-2,4-diaminoalkylbenzene (IV) is converted with the corresponding $C_2$- to $C_4$-chloroformic acid chloroalkyl ester to produce the hydroxyalkylated compounds of the general formula (Ia) according to the invention, where $R^2$ is a straight-chain or branched $C_2$- to $C_4$-hydroxyalkyl group and R and X are defined as indicated in the preceding:

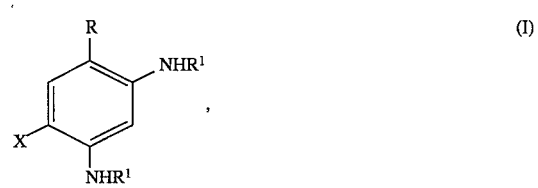

2. The compounds of formula (Ib), according to the invention, in which the amino groups are substituted with a straight-chain or branched $C_1$- to $C_4$-alkyl group can be produced from the corresponding 5-halogen-2, 4-diaminoalkylbenzenes (IV) in three synthesis steps according to the following diagram by converting with a conventional protective group reagent for amino groups, e.g. benzenesulfonyl chloride, alkylation with a conventional alkylating reagent, e.g. $C_1$- to $C_4$-alkyl iodides and subsequent elimination of the protective groups, where $R^3$ is a straight-chain or branched $C_1$- to $C_4$-alkyl group and Y is a conventional protective group for amino groups, and R and X are defined as indicated in the preceding:

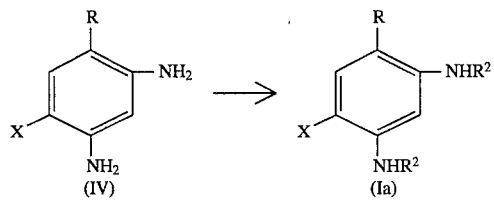

Further, the subject matter of the present application is a new 5-halogen-2,4-bis(alkylamino)-1-alkylbenzene of the general formula where R is a straight-chain or branched $C_1$- to $C_4$-alkyl group, X is chlorine or fluorine, and $R^1$ is a straight-chain or branched $C_1$- to $C_4$-alkyl group or a straight-chain or branched $C_2$- to $C_4$-hydroxyalkyl group.

Examples of the new compounds of formula (I) are 5-fluoro-2,4-bis(methylamino)toluene, 5-fluoro-2,4-bis-(ethylamino)toluene, 5-fluoro-2,4-bis[(2'-hydroxyethyl)amino]toluene and 5-chloro-2,4-bis[(2'-hydroxyethyl)amino]toluene.

The following examples will explain the subject matter of the invention in more detail.

EXAMPLES

| Example 1: | Hair dye composition in gel form |
|---|---|
| 0.22 g | 5-fluoro-2,4-bis(methylamino)toluene |
| 1.10 g | 2-(2'-hydroxyethyl)-1,4-diaminobenzene sulfate |
| 0.20 g | resorcinol |
| 0.05 g | m-aminophenol |
| 0.40 g | sodium sulfite, anhydrous |
| 15.00 g | oleic acid |
| 7.00 g | isopropanol |
| 10.00 g | ammonia (22-percent aqueous solution) |
| 66.03 g | water |
| 100.00 g | |

50 g of this hair dye composition in gel form are mixed with 50 ml of 6-percent hydrogen peroxide solution shortly before application. The mixture is then applied to blond human hair. After allowing it to act for a period of thirty minutes at 40 degrees Celsius, the hair is rinsed with water and dried. The hair is dyed a natural medium-blonde.

| Example 2: | Hair dye composition in gel form |
|---|---|
| 0.27 g | 5-fluoro-bis(ethylamino)toluene |
| 2.80 g | 2-methyl-p-phenylenediamine |
| 0.12 g | 3-aminophenol |
| 0.60 g | 4-hydroxy-1,2-methylenedioxybenzene |
| 0.10 g | 3,5-diamino-2,6-dimethoxypyridine dihydrochloride |
| 0.40 g | sodium sulfite, anhydrous |
| 15.00 g | oleic acid |
| 7.00 g | isopropanol |
| 10.00 g | ammonia (22-percent aqueous solution) |
| 63.71 g | water |
| 100.00 g | |

50 g of this hair dye composition in gel form are mixed with 50 ml of 6-percent hydrogen peroxide solution shortly before application. The mixture is then applied to blond human hair. After allowing it to act for a period of thirty minutes at 40 degrees Celsius, the hair is rinsed with water and dried. The hair is dyed a natural dark brown.

| Example 3: | Hair dye solution |
|---|---|
| 0.20 g | 5-fluoro-2,4-bis[(2'-hydroxyethyl)-amino]toluene |
| 0.80 g | p-aminophenol |
| 0.12 g | resorcinol |
| 0.10 g | m-aminophenol |
| 1.05 g | 5-amino-2-methylphenol |
| 0.40 g | sodium sulfite, anhydrous |
| 10.00 g | lauryl alcohol diglycol ether sulfate (28-percent aqueous solution) |
| 10.00 g | isopropanol |
| 20.00 g | ammonia (22-percent aqueous solution) |
| 57.33 g | deionized water |
| 100.00 g | |

50 g of this hair dye solution are mixed with 50 ml of 6-percent hydrogen peroxide solution shortly before application. The mixture is then applied to blond human hair. After allowing it to act for a period of thirty minutes at 40 degrees Celsius, the hair is rinsed with water and dried. The hair is dyed a gold-orange.

| Example 4: | Hair dye solution |
|---|---|
| 0.61 g | 5-chloro-2,4-bis[(2'hydroxyethyl)-amino]toluene |
| 0.15 g | 4-amino-3-methylphenol |
| 0.14 g | 4-aminophenol |
| 0.40 g | sodium sulfite, anhydrous |
| 10.00 g | lauryl alcohol diglycol ether sulfate (28-percent aqueous solution) |
| 10.00 g | isopropanol |
| 20.00 g | ammonia (22-percent aqueous solution |
| 58.70 g | deionized water |
| 100.00 g | |

50 g of this hair dye solution are mixed with 50 ml of 6-percent hydrogen peroxide solution shortly before application. The mixture is then applied to blond human hair. After allowing it to act for a period of thirty minutes at 40 degrees Celsius, the hair is rinsed with water and dried. The hair is dyed a fashionable wine-red shade.

Comparison Examples

To compare the color intensities in the red range, one of the couplers of the general formula (I) according to the invention 5-fluoro-2,4-bis(methylamino)toluene
5-fluoro-2,4-bis(ethylamino)toluene
5-fluoro-2,4-bis[(2'-hydroxyethyl)amino]toluene
5-chloro-2,4-bis[(2'-hydroxyethyl)amino]toluene
or the known coupler
2,4-diamino-5-tetrafluoroethoxytoluene
in combination with an equimolar amount of one of the known developers

| 4-aminophenol | (Examples I, III, V, VII, IX) |
|---|---|
| or | |
| 4-amino-3-methylphenol | (Examples II, IV, VI, VIII, X) | are used as dyes in a hair dye solution.

| Example I: | Dye solution |
|---|---|
| 10.0000 g | mixture of the potassium salts of coconut fatty acid and oleic acid |
| 10.0000 g | isopropanol |
| 1.9125 g | 5-fluoro-2,4-bis(methylamino)toluene |
| 1.3630 g | 4-aminophenol |
| 10.0000 g | ammonia (25-percent aqueous solution) |
| 66.7245 g | water |
| 100.0000 g | |

| Example II: | Dye solution |
|---|---|
| 10.0000 g | mixture of the potassium salts of coconut fatty acid and oleic acid |
| 10.0000 g | isopropanol |
| 1.9125 g | 5-fluoro-2,4-bis(methylamino)toluene |
| 1.5380 g | 4-amino-3-methylphenol |
| 10.0000 g | ammonia (25-percent aqueous solution) |
| 66.5495 g | water |
| 100.0000 g | |

| Example III: | Dye solution |
|---|---|
| 10.0000 g | mixture of the potassium salts of coconut fatty acid and oleic acid |
| 10.0000 g | isopropanol |
| 2.2625 g | 5-fluoro-2,4-bis(methylamino)toluene |
| 1.3630 g | 4-amino-3-methylphenol |
| 10.0000 g | ammonia (25-percent aqueous solution) |
| 66.3745 g | water |
| 100.0000 g | |

| Example IV: | Dye solution |
|---|---|
| 10.0000 g | mixture of the potassium salts of coconut fatty acid and oleic acid |
| 10.0000 g | isopropanol |
| 2.2625 g | 5-fluoro-2,4-bis(methylamino)toluene |
| 1.5380 g | 4-amino-3-methylphenol |
| 10.0000 g | ammonia (25-percent aqueous solution) |
| 66.1995 g | water |
| 100.0000 g | |

| Example V: | Dye solution |
|---|---|
| 10.0000 g | mixture of the potassium salts of coconut fatty acid and oleic acid |
| 10.0000 g | isopropanol |
| 2.2625 g | 5-fluoro-2,4-bis[(2'-hydroxyethyl)-amino]toluene |
| 1.3630 g | 4-aminophenol |
| 10.0000 g | ammonia (25-percent aqueous solution) |

-continued

| | |
|---|---|
| 66.3745 g | water |
| 100.0000 g | |

| Example VI: | Dye solution |
|---|---|
| 10.0000 g | mixture of the potassium salts of coconut fatty acid and oleic acid |
| 10.0000 g | isopropanol |
| 2.2625 g | 5-fluoro-2,4-bis[(2'-hydroxyethyl)-amino]toluene |
| 1.5380 g | 4-amino-3-methylphenol |
| 10.0000 g | ammonia (25-percent aqueous solution) |
| 66.1995 g | water |
| 100.0000 g | |

| Example VII: | Dye solution |
|---|---|
| 10.0000 g | mixture of the potassium salts of coconut fatty acid and oleic acid |
| 10.0000 g | isopropanol |
| 2.8625 g | 5-fluoro-2,4-bis[(2'-hydroxyethyl)-amino]toluene |
| 1.3630 g | 4-aminophenol |
| 10.0000 g | ammonia (25-percent aqueous solution) |
| 65.7745 g | water |
| 100.0000 g | |

| Example VIII: | Dye solution |
|---|---|
| 10.0000 g | mixture of the potassium salts of coconut fatty acid and oleic acid |
| 10.0000 g | isopropanol |
| 2.8625 g | 5-chloro-2,4-bis[(2'-hydroxyethyl)-amino]toluene |
| 1.5380 g | 4-amino-3-methylphenol |
| 10.0000 g | ammonia (25-percent aqueous solution) |
| 65.5995 g | water |
| 100.0000 g | |

| Example IX: | Dye solution according to the prior art. |
|---|---|
| 10.0000 g | mixture of the potassium salts of coconut fatty acid and oleic acid |
| 10.0000 g | isopropanol |
| 2.9625 g | 2,4-diamino-5-tetrafluorethoxytoluene |
| 1.3630 g | 4-aminophenol |
| 10.0000 g | ammonia (25-percent aqueous solution) |
| 65.6745 g | water |
| 100.0000 g | |

| Example X: | Dye solution according to the prior art |
|---|---|
| 10.0000 g | mixture of the potassium salts of coconut fatty acid and oleic acid |
| 10.0000 g | isopropanol |
| 2.9625 g | 2,4-diamino-5-tetrafluorethoxytoluene |
| 1.5380 g | 4-amino-3-methylphenol |
| 10.0000 g | ammonia (25-percent aqueous solution) |
| 65.4995 g | water |
| 100.0000 g | |

5 g of the dye solutions of Examples I to X were mixed with 5 g 6-percent hydrogen peroxide solution shortly before application. The mixture was then applied to white buffalo hair strands. After allowing the mixture to act for a period of 30 minutes at 40° C., the buffalo hair strands were rinsed with water and dried.

Finally, the color values of the dyed buffalo hair strands were determined by a color measuring device (Chromameter CR 200 by Minolta). In the following table, Y represents the brightness compared to a pure white surface (Y=100%), i.e. the greater the value of Y, the brighter the dyeing.

The parameters x, y and z represent the red, green and blue component of the shade in question, where x and y are measured and z can be calculated by the formula z=1−(x+y).

The color values of the dyed buffalo hair strands are indicated in Table 1:

TABLE 1

| | Color values | | | |
|---|---|---|---|---|
| dye solution | y | x | y | z |
| Example I | 5.5 | 0.417 | 0.303 | 0.280 |
| Example III | 6.0 | 0.400 | 0.293 | 0.307 |
| Example V | 6.8 | 0.394 | 0.287 | 0.319 |
| Example VII | 9.3 | 0.382 | 0.297 | 0.321 |
| Example IX | 35.8 | 0.355 | 0.333 | 0.312 |
| Example II | 6.4 | 0.363 | 0.270 | 0.367 |
| Example IV | 9.5 | 0.344 | 0.267 | 0.389 |
| Example VI | 8.7 | 0.343 | 0.260 | 0.397 |
| Example VIII | 14.1 | 0.340 | 0.278 | 0.382 |
| Example X | 49.8 | 0.334 | 0.332 | 0.324 |

The comparison colorings show that the depth of color achieved with the dye solutions (Examples I to VIII) containing the compounds (couplers) of the general formula (I) according to the invention is clearly higher (=lower Y values) compared to the dye solutions (Examples IX to X) containing the known couplers.

Example A

Production of 5-fluoro-2,4-bis(methylamino)toluene

Step 1: 5-Fluoro-2,4-dinitrotoluene 5.5 g fluorotoluene are nitrated with a cooled mixture of 10.9 ml concentrated $H_2SO_4$ and 9.3 ml concentrated $HNO_3$. The mixture is stirred at room temperature for 24 hours and then poured over ice. The precipitate is removed by suction and washed with water. After recrystallizing from ethanol, 5.8 g (58% of theory) pale yellow crystals with a melting point of 80° Celsius are obtained.

$^1$H-NMR ($D_6$-DMSO): δ=2.64 (s; 3H, —$CH_3$) 7.85 (d, J=12 Hz; 1H, 6-H) 8.76 ppm (d, J=7.1 Hz; 1H, 3-H)

MS (70 eV): m/e=200 ($M^+$)

Step 2: 5-Fluoro-2,4-diaminotoluene 2 g (0.01 ml) 5-fluoro-2,4-dinitrotoluene from Step 1 are hydrated with catalytic amounts of palladium/carbon (10% Pd) in 50 ml absolute ethanol. After removing the catalyst by filtration, the solvent is completely removed by distillation and the obtained product is recrystallized from toluene. 0.7 g (50% of theory) 5-fluoro-2,4-diaminotoluene are obtained which melts at 112° C. accompanied by decomposition.

$^1$H-NMR ($D_6$-DMSO): δ=2.49 (s; 3H, —$CH_3$) 4.36 (s; 2H, $NH_2$) 4.54 (s; 2H, $NH_2$) 6.03 (d; J=8.6 Hz; 3-H) 6.54 ppm (d; J=12 Hz; 6-H)

MS (70 eV): m/e=140 ($M^+$)

Step 3: 5-Fluoro-2,4-bis[(N-benzenesulfonyl)amino]toluene 8 g 5-fluoro-2,4-diaminotoluene from Step 2 are dissolved in 250 ml pyridine, mixed with 7.9 ml benzenesulfonyl chloride, and stirred for 1 hour at 120° C. After cooling, the reaction preparation is poured over ice. The obtained precipitate is washed with water, dried in vacuum over phosphorus pentoxide, and recrystallized from methanol. 3.9 g (41% of theory) 5-fluoro-2,4-bis[(N-benzenesulfonyl)amino]toluene are obtained which melts at 146° C.

Step 4: 5-Fluoro-2,4-bis[(N-benzenesulfonyl,N-methyl)amino]toluene 3 g 5-fluoro-2,4-bis[(N-benzenesulfonyl)amino]toluene are heated with 0.9 g potassium hydroxide in 24 ml of a 1:1 mixture of water and ethanol to 30° C. At this temperature, 1.78 ml methyl iodide are added. The reaction preparation is stirred for 2 hours at 45° C. and then poured over ice. The precipitate is filtered out and recrystallized from a mixture of ethanol and water. 2.8 g (87% of theory) 5-fluoro-2,4-bis[(N-benzenesulfonyl,N-methyl)amino]toluene are obtained in the formal of beige crystals with a melting point of 148° C.

Step 5: 5-Fluoro-2,4-bis(methylamino)toluene 5 g 5-fluoro-2,4-bis[(N-benzenesulfonyl,N-methyl)amino]toluene are stirred in a mixture of 20 ml glacial acetic acid and 20 ml concentrated sulfuric acid for 20 minutes at 140° C. The reaction preparation is then poured on ice. The pH is adjusted to slightly alkaline with aqueous caustic soda and the precipitate is removed by suction. After drying the precipitate, 1.2 g 5-fluoro-2,4-bis(methylamino)toluene (62% of theory) with a melting point of 60° C. are obtained.

$^1$H-NMR ($D_6$-DMSO): $\delta$=1.93 (s; 3H, —$CH_3$), 2.50 (s; 2H, —$NCH_3$), 2.81 (s; 3H, —$NCH_3$), 4.61 (br. s; 1H, —NH, exchanged with $D_2O$), 4.96 (br. s; 1H, —NH, exchanged with $D_2O$), 5.79 (d, J=8.1 Hz; 1H, 3-H) and 6.63 ppm (d, J=12.4 Hz; 1H, 6-H)

MS (70 eV): m/e=168 ($M^{30}$)

Example B

Production of 5-fluoro-2,4-bis(ethylamino)toluene

Steps 1, 2 and 3: 5-fluoro-2,4-bis[(N-benzenesulfonylamino]toluene 5-fluoro-2,4-bis[(N-benzenesulfonyl)amino]toluene is produced from 3-fluorotoluene according to Steps 1, 2 and 3 described in Example A.

Step 4: 5-Fluoro-2,4-bis[(N-benzenesulfonyl-N-ethyl)amino]toluene 5 g 5-fluoro-2,4-bis[(N-benzenesulfonyl)amino]toluene from Step 3 are heated with 0.9 g potassium hydroxide in 24 ml of a 1:1 mixture of water and ethanol to 30° C. At this temperature, 3.22 ml ethyl iodide are added. The reaction preparation is stirred for 2 hours at 55° C. and then poured over ice. The precipitate is filtered and recrystallized from a mixture of ethanol and water. 2.6 g (46% of theory) 5-fluoro-2,4-bis[(N-benzenesulfonyl-N-ethyl)amino]toluene are obtained in the form of beige crystals with a melting point of 120° C.

Step 5: 5-Fluoro-2,4-bis(ethylamino)toluene 2 g 5-fluoro-2,4-bis[(N-benzenesulfonyl,N-ethyl)amino]toluene are stirred in a mixture of 8 ml glacial acetic acid and 8 ml concentrated sulfuric acid for 20 minutes at 140° C. The reaction preparation is then poured on ice. The pH is adjusted to slightly alkaline with aqueous caustic soda and the precipitate is removed by suction. After drying the precipitate, 0.4 g 5-fluoro-2,4-bis(ethylamino)toluene (54% of theory) are obtained in the form of colorless crystals with a melting point of 50° C.

$^1$H-NMR ($D_6$-DMSO): $\delta$=1.16 (t, J=7.4 Hz; 3H, —$CH_2$—$CH_3$), 1.18 (t, J=7.4 Hz; 3H, —$CH_2$—$CH_3$), 1.94 (s; 3H, —$CH_3$), 3.03–3.09 (q, J=6 Hz; 4H, —$CH_2$—$CH_3$), 4.23 (br. s; 1H, —NH, exchanged with $D_2O$), 4.68 (br. s; 1H, —NH, exchanged with $D_2O$), 5.87 (d, J=8.1 Hz; 1H, 3-H) and 6.39 ppm (d, J=12.4 Hz; 1H, 6-H)

MS (70 ev): m/e=196 ($M^+$)

Example C

Production of 5-fluoro-2,4-bis[(2'-hydroxyethyl)amino]toluene

Steps 1, 2: 5-Fluoro-2,4-diaminotoluene

5-Fluoro-2,4-diaminotoluene is produced from 3-fluorotoluene according to Steps 1 and 2 described in Example A.

Step 3: 5-Fluoro-2,4-bis[(2'-hydroxyethyl)amino]toluene 0.56 g 5-fluoro-2,4-diaminotoluene are heated to 70° C. with 0.66 g calcium carbonate in 20 ml dioxane, mixed with 1 ml chloroformic acid chloroethyl ester, and heated for 3 hours at 100° C. Filtration is effected accompanied by heat and the yellow filtrate is poured over 200 ml ice water. The precipitate is filtered and recrystallized from a mixture of ethanol and water.

0.5 g of the recrystallized precipitate are mixed with a mixture of 0.42 g potassium hydroxide in 5.6 ml ethanol and 2.4 ml water and heated for 1 hour under reflux. After cooling, the solution is diluted with water, neutralized with acetic acid and extracted with acetic acid.

0.21 g 5-fluoro-2,4-bis[(2'-hydroxyethyl)amino]toluene (35% of theory) are obtained in the form of black crystals with a melting point of 88° C. by chromatography on silica gel 60 with a grain size of 0.5 to 2 mm with a 1:1 mixture of chloroform and methanol and reduction of the eluate.

$^1$H-NMR ($D_6$-DMSO): $\delta$=1.95 (s; 3H, —$CH_3$), 3.10–3.14 (m; 4H, —$CH_2$—OH), 3.59 (m; 4H, —NH—$CH_2$), 4.25 (br. s; 1H, —OH, exchanged with $D_2O$), 4.65 (br. s; 1H, —OH, exchanged with $D_2O$), 4.72 (br. s; 2H, —NH, exchanged with $D_2O$), 5.95 (d, J=8.1 Hz; 1H, 3-H) and 6.65 ppm (d, J=12.3 Hz; 1H, 6-H)

MS (70 ev): m/e=228 ($M^{30}$)

Example D

Production of 5-chloro-2,4-bis[(2'-hydroxyethyl)amino]toluene

Step 1: 5-Chloro-2,4-diaminotoluene

5-Chloro-2,4-diaminotoluene is produced by the process described in F. Reverdin, P. Crépieux, Chemische Berichte 33, (1900), 2505 to 2508.

Step 2: 5-Chloro-2,4-bis[(2'-hydroxyethyl)amino]toluene 0.8 g 5-chloro-2,4-diaminotoluene are heated to 70° C. with 0.85 g calcium carbonate in 26 ml dioxane, mixed with 1.3 ml chloroformic acid ethyl ester, and heated for 3 hours at 100° C. Filtration is effected accompanied by heat and the yellow filtrate is poured over 256 ml ice water. The precipitate is filtered and recrystallized from a mixture of ethanol and water.

0.64 g of the recrystallized precipitate are mixed with a mixture of 0.54 g potassium hydroxide in 7.2 ml ethanol and 3 ml water and heated for 1 hour under reflux. After cooling, the solution is diluted with water, neutralized with acetic acid and extracted with acetic acid ethyl ester. 0.12 g 5-chloro-2,4-bis[(2'-hydroxyethyl)amino]toluene (18% of theory) are obtained in the form of brown crystals with a melting point of 83° C. by chromatography of the acetic acid ethyl ester extract on silica gel 60 with a grain size of 0.5 to 2 mm with a 1:1 mixture of chloroform and methanol and subsequent reduction of the eluate.

$^1$H-NMR ($D_6$-DMSO): $\delta$=1.94 (s; 3H, —$CH_3$), 3.57–3.62 (m; 4H, —NH—$CH_2$—), 4.58 (t, J=5.5 Hz; 1H; —OH, exchanged with $D_2O$) 4.67 (t, J =5.6 Hz; 1H; —OH, exchanged with $D_2O$) 4.75 (t, J=5.5 Hz; 1H; —NH, exchanged with $D_2O$) 4.80 (t, J=5.3 Hz; 1H; —NH, exchanged with $D_2O$) 5.92 (s; 1H, 3-H) and 6.82 ppm (s; 1H, 6-H)

MS (70 eV): m/e=244 ($M^{30}$)

All of the percentages indicated in the present application are percent by weight unless otherwise indicated.

We claim:
1. Composition for oxidative dyeing of hair, said composition containing, in respective amounts sufficient for the dyeing of hair, at least one developer and at least one coupler of the formula

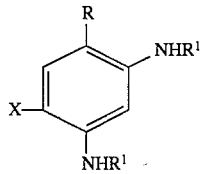

wherein R is a straight-chain or branched $C_1$- to $C_4$-alkyl group, X is selected from the group consisting of chlorine and fluorine, and $R^1$ is selected from the group consisting of straight-chain $C_1$- to $C_4$-alkyl groups, branched $C_1$- to $C_4$-alkyl groups, straight-chain $C_2$- to $C_4$-hydroxyalkyl groups and branched $C_2$- to $C_4$-hydroxyalkyl groups;

or a physiologically tolerated water-soluble salt thereof.

2. Composition according to claim 1, containing 0.01 to 5 percent by weight of said at least one coupler of the formula (I).

3. Composition according to claim 1, wherein said at least one coupler is selected from the group consisting of 5-fluoro-2,4-bis-(methylamino)toluene, 5-fluoro-2,4-bis-(ethylamino)toluene, 5-fluoro-2,4-bis[(2'-hydroxyethyl)amino]toluene and 5-chloro-2,4-bis[(2'-hydroxyethyl)amino]toluene.

4. Composition according to claim 1, further comprising at least one other coupler selected from the group consisting of resorcinol, 4-chlororesorcinol, 4,6-dichlororesorcinol, 2-methylresorcinol, 2-amino-4-(2'-hydroxyethylamino)anisole, 2-amino- 4-ethylaminoanisole, 2,4-diaminobenzyl alcohol, m-phenylenediamine, 5-amino-2-methylphenol, 2,4-diaminophenoxyethanol, 1-naphthol, m-aminophenol, 3-amino-4-chloro-6-methylphenol, 3-amino-2-methylphenol, 4-amino-2-hydroxyphenoxyethanol, 4-hydroxy-1,2-methylenedioxybenzene, 4-(2'-hydroxy-ethylamino)- 1,2-methylenedioxybenzene, 2,4-diamino- 5-ethoxytoluene, 4-hydroxyindole, 3-amino-5-hydroxy-2,6-dimethoxypyridine and 3,5-diamino-2,6-dimethoxypyridine.

5. Composition according to claim 1, wherein said at least one developer is selected from the group consisting of 1,4-diaminobenzene, 2,5-diaminotoluene, 2,5-diaminobenzyl alcohol, 2-(2'-hydroxyethyl)-1,4-diaminobenzene, 4-aminophenol, 4-amino-2-aminomethylphenol, 4-amino-3-methylphenol, 4-amino-2-methoxymethylphenol, 4-amino-2-ethoxymethylphenol, tetraaminopyrimidine and physiologically tolerated salts thereof.

6. Composition according to claim 1, containing a total quantity of said at least one developer and said at least one coupler amounting to 0.1 to 5.0 percent by weight.

7. Composition according to claim 1, further comprising a dye component selected from the group consisting of 6-amino-2-methylphenol and 2-amino-5-methylphenol, 4-{(4'-aminophenyl)-4"-imino-2",5"-cyclohexadien-1"-yliden)methyl}-2-methylaminobenzene monohydrochloride, 4-{(4'-amino-3'methylphenyl)-(4"-imino-3"-methyl-2",5"-cyclohexadien-1"-yliden)methyl}-2-methylaminobenzene monohydrochloride, 2-nitro-1,4-diaminobenzene, 2-amino-4-nitrophenol, 2-amino-5-nitrophenol, 2-amino-4,6-dinitrophenol, 2-amino-5-(2'-hydroxyethylamino)nitrobenzene, 4-(2'-hydroxyethylamino)-3-nitrotoluene, 1-(2'-ureidoethyl)amino-4-nitrobenzene, 7-{(4'-aminophenyl)azo}-8-hydroxynaphthalene 4-sulfonic acid sodium salt, 1,4-diaminoanthraquinone and 1,4,5,8-tetraaminoanthraquinone.

8. Composition according to claim 1, further comprising at least one conventional cosmetic ingredient selected from the group consisting of solvents; cationic, amphoteric and nonionic surfactants; and thickeners.

9. Composition according to claim 8, wherein said solvents include water, ethanol, propanol, isopropanol and glycols.

10. 5-Halogen-2,4-bis(alkylamino)-1-alkylbenzene compound of the formula

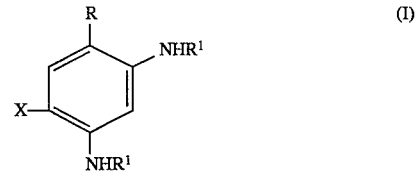

wherein R is a straight-chain or branched $C_1$- to $C_4$-alkyl group, X is selected from the group consisting of chlorine and fluorine, and $R^1$ is selected from the group consisting of straight-chain $C_1$- to $C_4$-alkyl groups, branched $C_1$- to $C_4$-alkyl groups, straight-chain $C_2$- to $C_4$-hydroxyalkyl groups and branched $C_2$- to $C_4$-hydroxyalkyl groups.

11. 5-fluoro-2,4-bis(methylamino)toluene.
12. 5-fluoro-2,4-bis(ethylamino)toluene.
13. 5-fluoro-2,4-bis[(2'-hydroxyethyl)amino]toluene.
14. 5-chloro-2,4-bis[(2'-hydroxyethyl)amino]toluene.

* * * * *